US 6,697,665 B1

(12) United States Patent
Rava et al.

(10) Patent No.: US 6,697,665 B1
(45) Date of Patent: Feb. 24, 2004

(54) SYSTEMS AND METHODS OF MOLECULAR SPECTROSCOPY TO PROVIDE FOR THE DIAGNOSIS OF TISSUE

(75) Inventors: Richard P. Rava, Waltham, MA (US); Joseph J. Baraga, Somerville, MA (US); Michael S. Feld, Waban, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 08/288,990

(22) Filed: Aug. 11, 1994

Related U.S. Application Data

(63) Continuation of application No. 07/661,077, filed on Feb. 26, 1991, now abandoned.

(51) Int. Cl.[7] .................................................. A61B 6/00
(52) U.S. Cl. ...................................................... 600/475
(58) Field of Search ................................ 600/473, 475; 436/63, 171, 172; 356/301

(56) References Cited

U.S. PATENT DOCUMENTS

| 3,327,117 | A | 6/1967 | Kamentsky |
| 3,327,119 | A | 6/1967 | Kamentsky |
| 3,461,856 | A | 8/1969 | Polanyi |
| 3,647,299 | A | 3/1972 | Lavallee |
| 4,213,462 | A | 7/1980 | Sato |
| 4,290,433 | A | 9/1981 | Alfano |
| 4,449,535 | A | 5/1984 | Renault |
| 4,479,499 | A | 10/1984 | Alfano |
| 4,515,165 | A | 5/1985 | Carroll |
| 4,556,057 | A | 12/1985 | Hiruma et al. |
| 4,641,650 | A | 2/1987 | Mok |
| 4,718,417 | A | 1/1988 | Kittrell et al. |
| 4,737,628 | A | 4/1988 | Lovoi |
| 4,758,081 | A | 7/1988 | Barnes |
| 4,768,516 | A | 9/1988 | Stoddart et al. |
| 4,894,547 | A | 1/1990 | Leffell et al. |
| 4,930,516 | A | 6/1990 | Alfano et al. |
| 4,975,581 | A | * 12/1990 | Robinson et al. ........... 128/633 |
| 4,981,138 | A | 1/1991 | Deckelbaum et al. |
| 5,115,137 | A | * 5/1992 | Andersson-Engels et al. ... 128/634 |
| 5,261,410 | A | * 11/1993 | Alfano et al. ................ 128/664 |
| 5,293,872 | A | * 3/1994 | Alfano et al. ................ 600/475 |

FOREIGN PATENT DOCUMENTS

| RU | 955709 | 12/1978 |
| WO | PCT/US84/00840 | 1/1984 |
| WO | PCT/US88/03257 | 9/1988 |
| WO | WO 89/02718 | * 4/1989 |

OTHER PUBLICATIONS

Nie et al., SPECTROSCOPY, vol. 5, No. 7—Applications of Near–Infrared Fourier Transform Raman Spectroscopy in Biology and Medicine.

Alfano et al. Lasers in the Life Sciences 4(1), 1991, pp. 23–28.

Human Breast Tissues Studied by IR Fourier Transform Raman Spectroscopy.

(List continued on next page.)

Primary Examiner—Ruth S. Smith
(74) Attorney, Agent, or Firm—Bowditch & Dewey, LLP

(57) ABSTRACT

Systems and methods for spectroscopic diagnosis and treatment are employed which utilize molecular spectroscopy to accurately diagnose the condition of tissue. Infrared Raman spectrscopy and infrared attenuated total reflectance measurements are performed utilizing a laser radiation source and a fourier transform spectrometer. Information acquired and analyzed in accordance with the invention provides accurate details of biochemical composition and pathologic condition.

8 Claims, 11 Drawing Sheets

OTHER PUBLICATIONS

Halaby et al. IEEE Transactions on Biomedical Engineering, vol. BME–26, No. 1 Jan. 1979. Computer–Controlled Spectral Measurements of Blood Cells.

Williamson et al., "Near–Infrared Raman Spectroscopy with a 783–nm Diode Laser and CCD Array Detector", *Applied Spectroscopy* vol. 43 No. 3, Mar. 1, 1989 pps. 372–375.

Ozaki, "Medical Application of Raman Spectroscopy" *Applied Spectoscopy Reviews,* vol 24, No. 3&4, Jul. 1, 1988, pps. 259–313.

Lewis et al., "Development of Near–Infrared Fourier Transform Raman Spectroscopy for the Study of Biologically Active Macromolecules", *Applied Spectroscopy,* vol. 42, No. 7, Sep./Oct. 1988 pps. 1188–1193.

Schwab et al., "Versatile, Efficient Raman Sampling with Fiber Optics", *Analytical Chemistry,* vol 56, No. 12, Oct. 1, 1984, pps. 2199–2201.

Ono et al., "Fiber optic reflectance spectrophotometry system for in vivo tissue diagnosis", *Applied Optics,* vol 30, No. 1, Jan. 1, 1991 pps. 98–105.

* cited by examiner

SYSTEMS AND METHODS OF MOLECULAR SPECTROSCOPY TO PROVIDE FOR THE DIAGNOSIS OF TISSUE

RELATED APPLICATION

This application is a continuation of application Ser. No. 07/661,077 filed on Feb. 26, 1991, now abandoned, which is incorporated herein by reference in its entirety.

GOVERNMENT SUPPORT

Funding for research conducted in connection with the subject matter of the present application was provided under NIH Grant No. RR 02594.

BACKGROUND OF THE INVENTION

In the United States heart attacks, almost entirely attributable to coronary atherosclerosis, account for 20–25% of all deaths. Several medical and surgical therapies are available for treatment of atherosclerosis; however, at present no in situ methods exist to provide information in advance as to which lesions will progress despite a particular medical therapy.

Objective clinical assessments of atherosclerotic vessels are at present furnished almost exclusively by angiography, which provides anatomical information regarding plaque size and shape as well the degree of vessel stenosis. The decision of whether an interventional procedure is necessary and the choice of appropriate treatment modality is usually based on this information. However, the histological and biochemical composition of atherosclerotic plaques vary considerably, depending on the stage of the plaque and perhaps also reflecting the presence of multiple etiologies. This variation may influence both the prognosis of a given lesion as well as the success of a given treatment. Such data, if available, might significantly assist in the proper clinical management of atherosclerotic plaques, as well as in the development of a basic understanding of the pathogenesis of atherosclerosis.

At present biochemical and histological data regarding plaque composition can only be obtained either after treatment, by analyzing removed material, or at autopsy. Plaque biopsy is contraindicated due to the attendant risks involved in removing sufficient arterial tissue for laboratory analysis. Recognizing this limitation, a number of researchers have investigated optical spectroscopic methods as a means of assessing plaque deposits. Such "optical biopsies" are non-destructive, as they do not require removal of tissue, and can be performed rapidly with optical fibers and arterial catheters. With these methods, the clinician can obtain, with little additional risk to the patient, information that is necessary to predict which lesions may progress and to select the best treatment for a given lesion.

Among optical methods, most attention has centered on ultraviolet and/or visible fluorescence. Fluorescence spectroscopy has been utilized to diagnose disease in a number of human tissues, including arterial wall. In arterial wall, fluorescence of the tissue has provided for the characterization of normal and atherosclerotic artery. However the information provided is limited by the broad line width of fluorescence emission signals. Furthermore, for the most part, fluorescence based methods provide information about the electromic structure of the constituent molecules of the sample. There is a need for non-destructive real time biopsy methods which provide more complete and accurate biochemical and molecular diagnostic information. This is true for atherosclerosis as well as other diseases which affect the other organs of the body.

SUMMARY OF THE INVENTION

The present invention relates to vibrational spectroscopic methods using Fourier transform infrared (FT-IR) attenuated total reflectance (ATR) and near-infrared (IR) FT-Raman spectroscopy. These methods provide extensive molecular level information about the pathogenesis of disease. Both of these vibrational techniques are readily carried out remotely using fiber optic probes. In particular, a preferred embodiment utilizes FT-Raman spectra of human artery for distinguishing normal and atherosclerotic tissue. Near IR FT-Raman spectroscopy can provide information about the tissue state which is unavailable from fluorescence methods. In situ vibrational spectroscopic techniques allow probing of the molecular level changes taking place during disease progression. The information provided is used to guide the choice of the correct treatment modality.

These methods include the steps of irradiating the tissue to be diagnosed with radiation in the infrared range of the electromagnetic spectrum, detecting light emitted by the tissue at the same frequency, or alternatively, within a range of frequencies on one or both sides of the irradiating light, and analyzing the detected light to diagnose its condition. Both the Raman and ATR methods are based on the acquisition of information about molecular vibrations which occur in the range of wavelengths between 3 and 300 microns. Note that with respect to the use of Raman shifted light, excitation wavelengths in the ultraviolet, visible and infrared ranges can all produce diagnostically useful information. Near IR FT-Raman spectroscopy is ideally suited to the study of human tissue.

Raman spectroscopy is an important method in the study of biological samples, in general because of the ability of this method to obtain vibrational spectroscopic information from any sample state (gas, liquid or solid) and the weak interference from the water Raman signal in the "fingerprint" spectral region. The FT-spectrometer furnishes high throughput and wavelength accuracy which might be needed to obtain signals from tissue and measure small frequency shifts that are taking place. Finally, standard quartz optical fibers can be used to excite and collect signals remotely.

Near IR FT-Raman spectroscopy provides the capability to probe biological substituents many hundred microns below the tissue surface. In particular, for atherosclerotic tissue, calcified deposits below the tissue surface are easily discerned. Thus, it becomes possible to detect pathologic conditions which would not be apparent using angioscopic methods, as well as to study the detailed molecular basis of the pathology.

In contrast with electronic techniques, the bands in a vibrational spectrum are relatively narrow and easy to resolve. Vibrational bands are readily assigned to individual molecular groups.

The ATR technique offers several features especially suited to sampling of human tissue in vivo. Being a surface technique, the ATR method can non-destructively probe internal human tissue either by direct contact in a hollow organ (e.g. artery), or by insertion of a needle probe. In the mid-IR region, strong water absorption dominates the spectra of highly hydrated samples such as arterial tissue, obscuring the absorption from other tissue components (see FIG. 4). Accurate subtraction of the strong water absorption from FT-IR ATR spectra is relatively easy and very reliable with the high dynamic range, linearity, stability, and wavelength precision of available FT spectrometers. Furthermore, high quality mid-IR spectra of aqueous protein solutions can be collected with fiber optic ATR probes. Such probes are easily adaptable to existing catheters for remote, non-destructive measurements in vivo. The mid-IR ATR technique allows clinicians to gather precise histological and biochemical data from a variety of tissues during standard catheterization procedures with minimal additional risk.

The present methods relate to infrared methods of spectroscopy of various types of tissue and disease including cancerous and pre-cancerous tissue, non-malignant tumors or lesions and atherosclerotic human artery. Examples of measurements on human artery generally illustrate the utility of these spectroscopic techniques for clinical pathology. Results obtained demonstrate that high quality, reproducible FT-IR ATR spectra of human artery can be obtained with relative ease and speed. In addition, molecular level details can be reliably deduced from the spectra, and this information can be used to determine the biochemical composition of various tissues including the concentration of molecular constituents that have been precisely correlated with disease states to provide accurate diagnosis.

Another preferred embodiment of the present invention uses two or more diagnostic procedures either simultaneously or sequentially collected to provide for a more complete diagnosis. These methods can include the use of fluorescence of endogeneous tissue, Raman shifted measurements and/or ATR measurements.

DETAILED DESCRIPTION

Figure 1A:
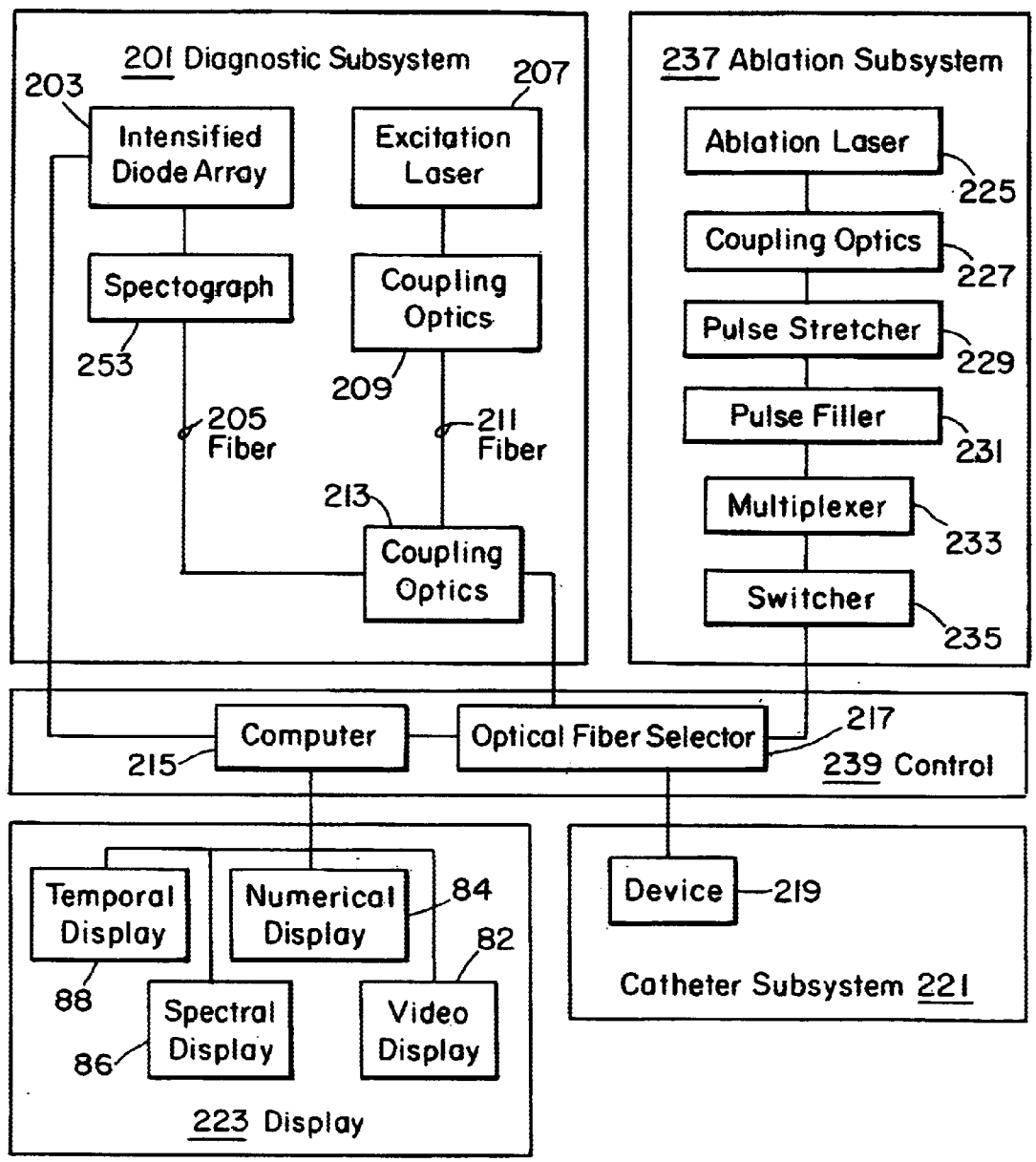
FIGS. 1A–1C are schematic illustrations of preferred systems for providing the spectroscopic measurements of the invention.

The spectroscopic methods of the present invention can be performed on a system such as that for laser treatment of atheroschlerosis which is illustrated in FIG. 1A. FIG. 1A includes separate block diagrams for the system of the invention which utilizes laser light for spectroscopic diagnosis as well as for treatment and/or removal of tissue. The ablation laser 225, pulse stretcher 229 and the pulse filler/multiplexer 231, 233 produce an output laser ablation pulse of sufficient energy and intensity to remove tissue and sufficient pulse duration to propagate through a fiber optic laser catheter delivery system without damaging the fibers. These systems and methods are more fully described in copending application U.S. Ser. No. 07/644,202 filed on Jan. 22, 1991, which is incorporated herein by reference.

Figure 1B:
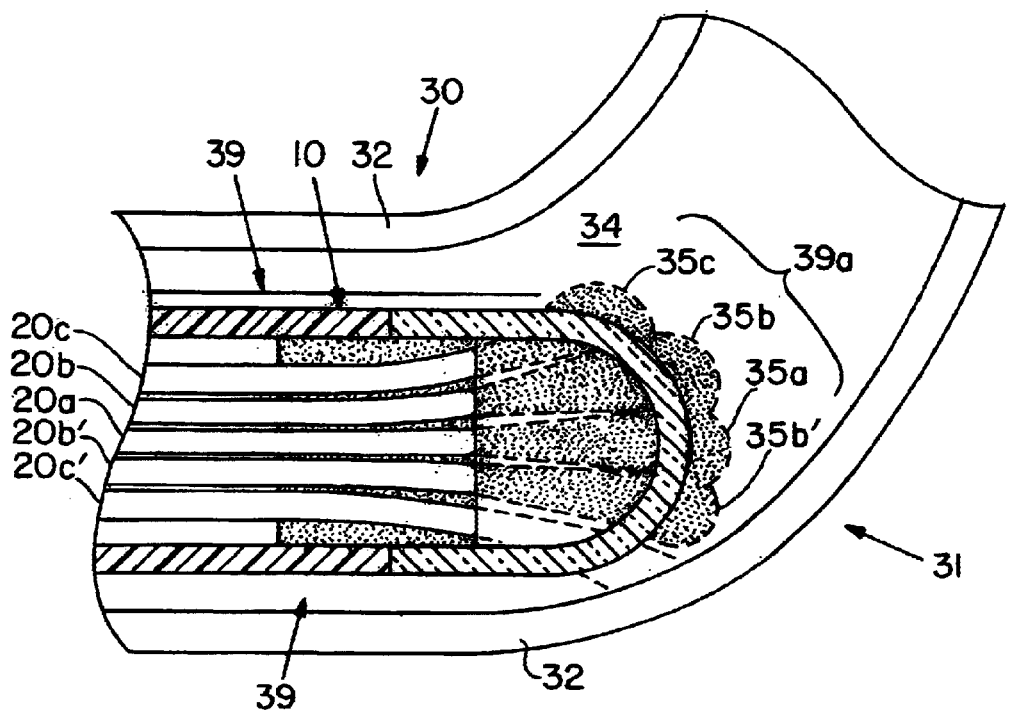

To remove plaque, a device 219 is used to contact the tissue such as multiple-fiber laser catheter 10 of FIG. 1B with an optical shield. The catheter 10 is inserted into the artery and the distal end of the catheter is brought into contact with the lesion. Next, a determination is made as to the type of tissue at which each optical fiber 20a–c' is aimed. Only fibers aimed at diseased tissue are activated. Thus, selective tissue removal is obtained.

The present invention relates to systems and methods of performing spectral diagnostics to diagnose the tissue in front of each fiber. In a preferred embodiment a laser light source 207 is coupled to the fibers. The diagnostic light is sent to the fiber of choice by the optical fiber selector 217.

The diagnostic light exits the selected optical fiber and falls on the tissue. The tissue absorbs the light and a fraction of the absorbed light is re-emitted, by Rayleigh fluorescence, Raman or other elastic or inelastic light scattering processes. This light is returned to the optical fibers and exits from selector 217, and is detected by a photodiode, photomultiplier or other detector 203. Diagnostic subsystem produces the entire spectral signal which is coupled to computer 215 from array 203.

The computer stores the information in a memory as a spectrum, which is a graph of light intensity vs. wavelength. This can be displayed immediately on the video display 82 or compared to an existing spectrum stored in the computer and the difference displayed on the spectral display 86.

Temporal display 88 can display corrections made for the wavelength dependent sensitivities of the source. Information from either the temporal or spectral display can be stored in the computer 215 from array 302. The comparative data is shown on numerical display 84 to provide a quantitative measure of the health of the tissue observed.

With a multichannel detector and a computer, or with appropriate multiple filters and detectors, it is possible to gather this information in a fraction of a second. Thus, a spectral or numerical display is provided which indicates the type of tissue at which the fiber of interest is aimed. If the tissue is plaque, and is to be removed, then fiber selector 217 will align this fiber with the output beam of the high power laser 225. Then, the high power laser 225 is turned on and an appropriate power level is selected for a predetermined amount of time to remove a certain amount of diseased tissue. The beam of laser 225 is transmitted to pulse stretcher 229 and pulse filler/multiplexer 231, 233 to properly adjust the beam fluence.

The procedure is repeated for different fibers. Where diseased tissue is detected, it is quickly removed. The laser catheter 10 nibbles away at the plaque, leaving the healthy artery wall intact.

If the artery 30 makes a bend 31 as shown by FIG. 1B, the laser catheter 10 will tend to make contact with artery wall 32 at the outside wall of the bend. To prevent the catheter from contacting the artery wall, the optical fiber 20c is not fired. The lesion is removed asymmetrically. This allows the laser catheter 10 to follow the lumen 39, 39a around the bend. Thus, the artery wall 32 is not irradiated and is not perforated. Additional details of this fiber optic catheter 10 are disclosed in U.S. Pat. No. 4,913,142, the contents of which are incorporated herein by reference.

In both Raman and ATR methods, information is contained in the spectral lines which are observed in their intensities, and also their linewidths and center frequencies (and how they change in different environments). Further, Raman and infrared ATR have different "selection rules". Some vibrations seen in infrared ATR won't show up in Raman, and vice versa. In other cases the same vibration can be detected by both techniques, but with different relative intensities (e.g. a strong Raman line will be weak in ATR). So in this sense the two techniques provide complementary information and combining the two techniques (or using either or both with laser induced fluorescence) is valuable in diagnosing pathology.

The methods utilize Fourier transform detection to observe the radiation thereby providing improved signal/noise ratios. Other techniques (e.g. diode array detection) can also be used.

As described in more detail below contributions from major tissue constituents can be "subtracted out" to reveal information about molecules which are present in small concentrations. For example, in ATR water contributions are removed before the "dry" tissue constituents could be studied. Also derivative spectroscopy is used to eliminate background signals. Note that these techniques deconvolute the observed spectra into its individual constituents, an essential step for optimal extraction of diagnostic information.

While Raman samples deeply into tissue, ATR samples only a very thin layer (a few microns). Thus, ATR is "naturally" suited to probe surface disease, such as the superficial cancers of the bladder and GI tract, whereas Raman is well suited to providing information about conditions deep inside tissue (such as breast cancer or stones). This is important for 3D imaging.

Generally, the ATR signal is very sensitive to the surface of the waveguide or probe. For example, if the probe surface has an affinity for lipids in the tissue, lipids can migrate to the probe surface, creating a thin lipid layer and producing a large signal. This can be a problem (it can give misleading information if not properly recognized and guarded against). Conversely, it can be used to advantage: Probes with special surfaces can be developed to prevent this effect or to promote it, in order to search for particular substances in the tissue.

In a preferred method one can adjust depth probed by ATR by varying refractive index of ATR probe. Alternatively as discussed below one can use a "waveguide needle" to get subsurface information.

Raman dianostic methods permit adjustment of Raman depth by varying the wavelength. Penetration depth is wavelength dependent, and can be varied by choosing different excitation wavelengths between about $\lambda=700$ nm and 2 $\mu$m. Another potentially important way of adjusting Raman depth is to vary the collection angle. In the near IR, incident (exciting) light is strongly scattered out of the forward direction into larger angles, so Raman signals sampled at smaller angles come from tissue closer to the surface. We have just obtained some experimental evidence for this.

Depth information is important if one desires to provide imaging by creating 3D images of small tumors in the brain or breast. Differential techniques based on the ideas of the preceding paragraph might allow accurate localization of such tumors in three dimensions. Near-IR Raman can be combined with a sound wave technique (time of flight or standing waves set up in the tissue)—the sound wave would modulate the Raman signal emanating from a point in the tissue when it passes that point, and the modulated signal could be used to establish the depth of the tissue producing the signal.

Figure 1C:
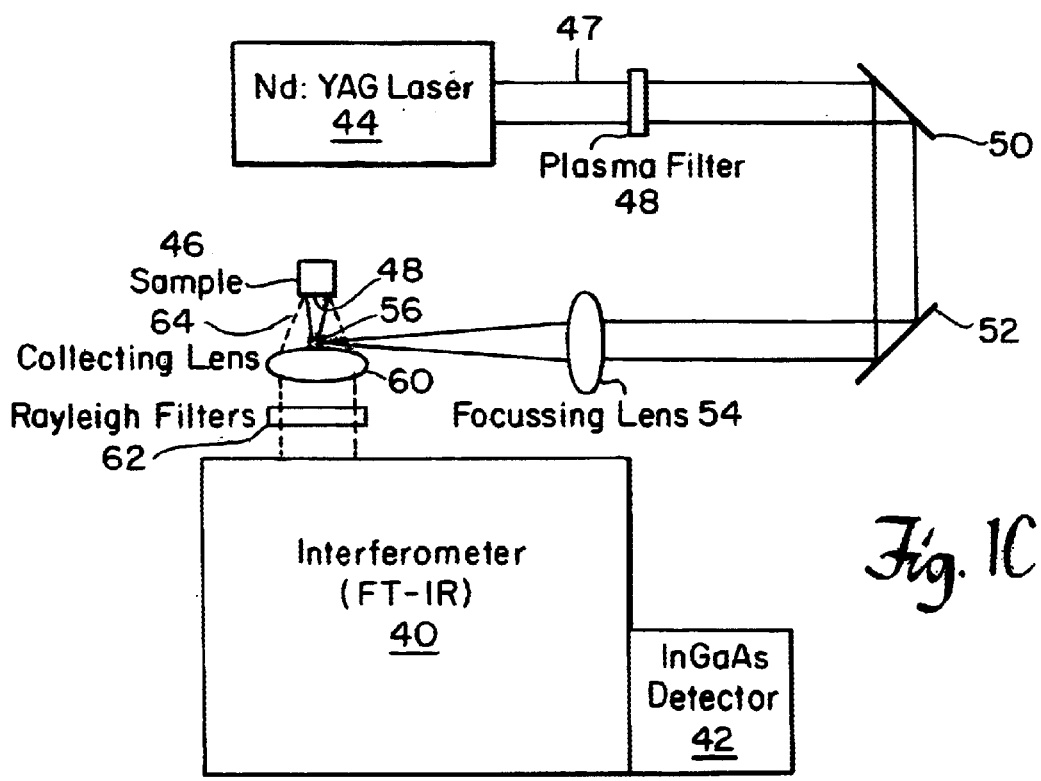

A system employed for the collection of Raman spectral data from excised tissue samples is illustrated in FIG. 1C. FT-Raman spectra were measured from 0–4000 cm$^{-1}$ above the laser excitation frequency with a FT-IR interferometer 40 equipped with a FT-Raman accessory. The accessory employed at 180° back scattering geometry and a cooled (77K) InGaAs detector 42.

A 1064 nm CW Nd:YAG laser 44 can be used for irradiating a sample 46: utilizing 1 W laser power in a 2.5 mm spot 48 at the sample 46 to collect Raman data. Alternatively, a pulsed laser source can also be employed. Laser 44 generated a beam 45 that is directed through plasma filter 48, mirrors 50, 52, focussing lens 54 and mirror or prism 56 before irradiating the sample 46. The radiation received by sample 46 undergoes various mechanisms of absorption, reflection and scattering including Raman scattering. Some of the light emitted by the tissue is directed toward lens 60 and then through one or more Rayleigh filters 62. The collecting lens 60 collects this backscattered light 64 and collimates it. The Rayleigh filters 62 removes the elastically scattered light and transmits the inelastically scattered, frequency shifted (Raman) light. The Raman scattered light enters the interferometer 40. No visible sample degradation was observed under these conditions.

Excised human aorta was chosen of atherosclerotic artery tissue. Samples were obtained at the time of post mortem examination, rinsed with isotonic saline solution (buffered at pH 7.4), snap-frozen in liquid nitrogen, and stored at −85° C. until use. Prior to spectroscopic study, samples were passively warmed to room temperature and were kept moist with the isotonic saline. Normal and atherosclerotic areas of tissue were identified by gross inspection, separated, and sliced into roughly 8×8 mm pieces.

The tissue samples were placed in a suprasil quartz cuvette with a small amount of isotonic saline to keep the tissue moist, with one surface in contact with the irradiated by the laser 44. The spectra shown in FIGS. 2 and 3 were collected with 512 scans at 8 cm$^{-1}$ resolution (approximately 35 minutes total collection time).

Human aorta is composed of three distinct layers: intima, media, and adventitia. The intima, normally less than 300 $\mu$m thick, is the innermost layer and provides a non-thrombogenic surface for blood flow. It is mainly composed of collagen fibers and ground substance. The medial layer, typically about 500 $\mu$m thick, is quite elastic and serves to smooth the pulsatile blood flow from the heart. The structural protein elastin is the major component of aortic media, with some smooth muscle cells present as well. The outermost adventitial layer serves as a connective tissue network which loosely anchors the vessel in place, and is mainly made up of lipids, lipoproteins and collagen. During the atherosclerotic process, the intima thickens due to collagen proliferation, fatty necrotic deposits accumulate under and within the collagenous intima, and eventually, calcium builds up, leading to calcium hydroxyapatite deposits in the artery wall.

Figure 2:
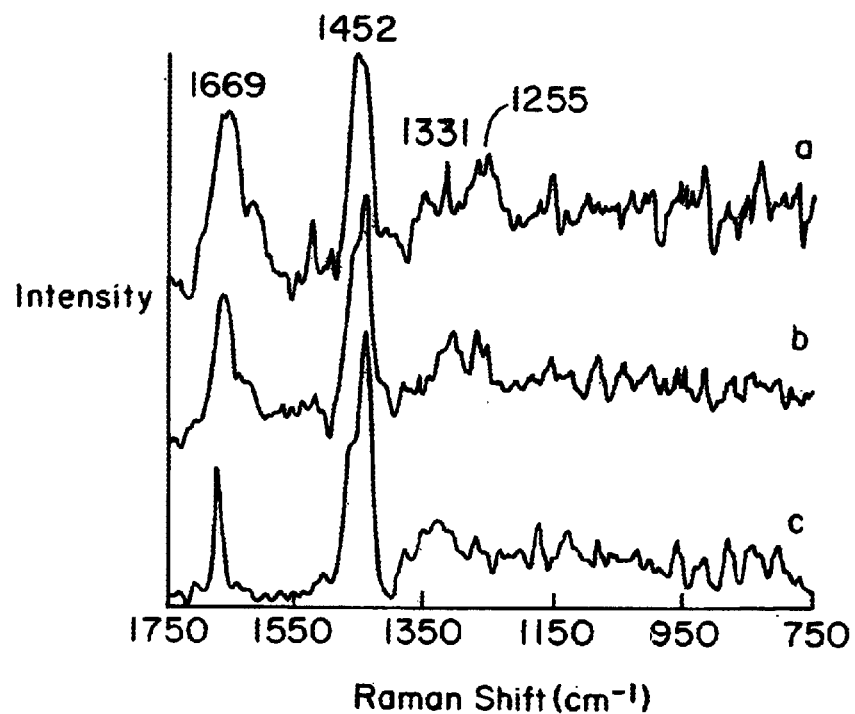
FIG. 2 graphically illustrates FT-Raman spectra of human aorta: a) normal artery; b) atheromatous plaque; c) FT-Raman spectrum solid cholesterol (Sigma).

FIG. 2, curve a, shows the FT-Raman spectrum of a full thickness section of aorta grossly identified as normal. Laser irradiation was on the intimal side. The dominant bands appear at 1669 cm$^{-1}$ and 1452 cm$^{-1}$ and can be assigned to an amide I backbone and C—H in-plane bending vibration from proteins, respectively. Weaker bands at 1331 and 1255 cm$^{-1}$ are assigned to C—H wagging and amide III vibrations from proteins, respectively. The frequencies of amide I and III are consistent with those observed for disordered proteins.

The FT-Raman spectrum obtained from a diseased artery, an atheromatous plaque, with a thick fibrous connective tissue cap and an underlying necrotic core is shown in FIG. 2, curve b. The necrotic core of an atheromatous plaque contains cellular debris as well as large accumulations of oxidized lipids and cholesterol. The band in the amide I region, peaking at 1665 cm$^{-1}$, is distinctly narrower in this spectrum compared to normal aorta. In addition, the in-plane C—H bend, at 1444 cm$^{-1}$, is relatively more intense and has a distinct shoulder at higher frequency. The two weaker bands at 1307 and 1267 cm$^{-1}$ are shifted in frequency from those found in the spectrum of normal aorta. The band frequencies and shapes in the FT-Raman spectrum of cholesterol, shown in FIG. 2, curve c, coincide with some of those observed in the atheromatous plaque, consistent with the expected composition of the necrotic core.

Figure 3:
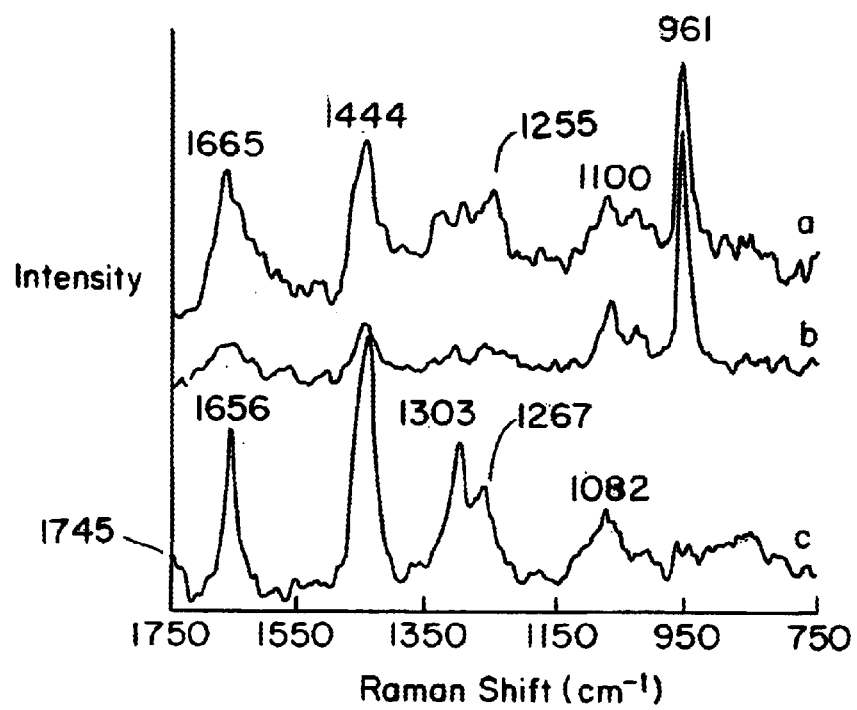
FIG. 3 graphically illustrates FT-Raman spectra of calcified human aorta: a) calcified with fibrous cap; b) excised calcification from a different plaque; c) spectra of the same tissue as in a) taken from adventitial side.

In an advanced plaque, calcium may begin to accumulate leading to the formation of calcium hydroxyapatite crystals in the tissue. The FT-Raman spectrum of a calcified plaque with a thick (several hundred microns) fibrous connective tissue cap overlying a calcified deposit is shown in FIG. 3, curve a, The spectrum clearly indicates bands due to the protein in the fibrous cap, amide I and III at 1665 and 1255 cm$^{-1}$, respectively. However, additional bands are observed between 1250 and 1350 cm$^{-1}$ and around 1100 cm$^{-1}$, as well as a strikingly sharp band at 961 cm$^{-1}$. The latter is readily assigned to the symmetric phosphate stretching vibration associated with phosphate groups in the calcium hydroxyapatite deposits, while the band around 1100 cm$^{-1}$ is an asymmetric phosphate stretch. These assignments are confirmed by excising the solid "rock" from a different calcified plaque, and obtaining its spectrum as shown in FIG. 3, curve b. A strong Raman signal from the phosphate stretching vibration in solid calcifications in advanced atherosclerotic plaques can also be observed utilizing standard visible Raman instrumentation. The ability to detect the calcifications several hundred microns below the tissue surface when using near IR FT-Raman spectroscopy, however, is a diagnostic measurement which can be utilized to guide treatment.

A measurement was attempted to determine if the calcification might be detected when the tissue was irradiated from the adventitial side. The resulting FT-Raman spectrum is shown in FIG. 3, curve c. No evidence of the strong phosphate vibration is apparent. In contrast, sharp vibrational bands at 1745, 1656, 1444, 1303, 1267 and 1082 cm$^{-1}$ are observed which are mainly associated with the lipid material that constitutes the majority of the adventitia.

The present methods provide an IR FT-Raman technique for differentiating various stages of atherosclerosis in human aorta. They demonstrate that molecular level information is available using these methods. This information is useful for following the pathogenesis of the disease and in guiding the treatment of different lesions. The near IR FT-Raman method, with its relatively deep penetration depth, is able to obtain spectroscopic signals from below the tissue surface, yielding details about the atheromatous necrotic tissue and sub-surface calcifications. These signals can be utilized with an optical fiber based imaging system to determine the content and composition of different atherosclerotic plaques in vivo.

A second spectroscopic method is also used to obtain molecular vibration information, attenuated total reflectane (ATR) of infrared light.

Human aorta was chosen as an example to illustrate the diagnosis of atherosclerotic artery tissue. As in the samples obtained for the Raman spectral measurements human aorta samples were obtained for ATR measurements at the time of post mortem examination. Sample storage and preparation procedures are identical to those set forth for the Raman spectral measurements. These reflectance measurements can be used by themselves to provide diagnostic data in conjunction with either the Raman spectroscopic measurements described above or with fluorescence measurements, or with both types of measurements to enhance diagnosis for specific applications.

The medial layers of a normal arteries and the necrotic cores of atheromatous plaques were exposed by blunt dissection and spectroscopically examined. ATR spectra were also collected from several purified tissue components including collagen, elastin, and cholesterol to assist in analysis of the spectra.

Mid-infrared ATR spectra were measured from 4000 to 700 cm$^{-1}$ with a commercially available FT-IR spectrometer and a horizontal ATR accessory. The sampling area was purged with dry nitrogen gas to control background absorption from atmospheric water vapor and $CO_2$. Spectra were collected at 4 cm$^{-1}$ resolution with 50 scans. The artery specimens, kept physiologically moist with isotonic saline (buffered at pH 7.4), were placed in contact with the ATR element (ZnSe crystal 45° ends). A 5 gram weight placed on the tissue sample ensured uniform sample contact with the ATR element. An ATR spectrum of the saline solution with absorbance similar to that of the artery samples was also obtained and used for subtraction of spectral components due to water. Collagen (Calbiochem: type I, bovine achilles tendon) and elastin (Sigma: bovine neck ligament) were prepared as saline slurries. Cholesterol (Sigma) was prepared as a dry film on the ATR element by evaporation of a benzene solution.

The ATR sampling crystal is a rod of high refractive index material which acts as a waveguide for the infrared sampling beam. This waveguide can be in the form of a needle that is adapted for penetration into the tissue to be diagnosed. Alternatively, the probe will have a geometry suitable for contacting the surface of exposed tissue sites or for contacting internal locations with a catheter.

Figure 12A:
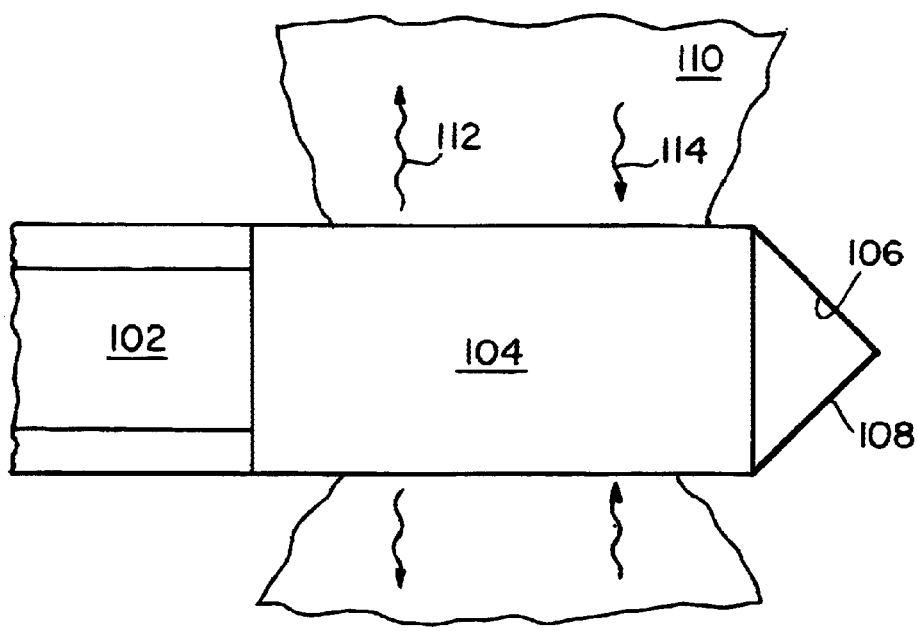
FIGS. 12A and 12B are additional preferred embodiments of ATR probes adapted to make the diagnostic measurements of the present invention.
Figure 12B:
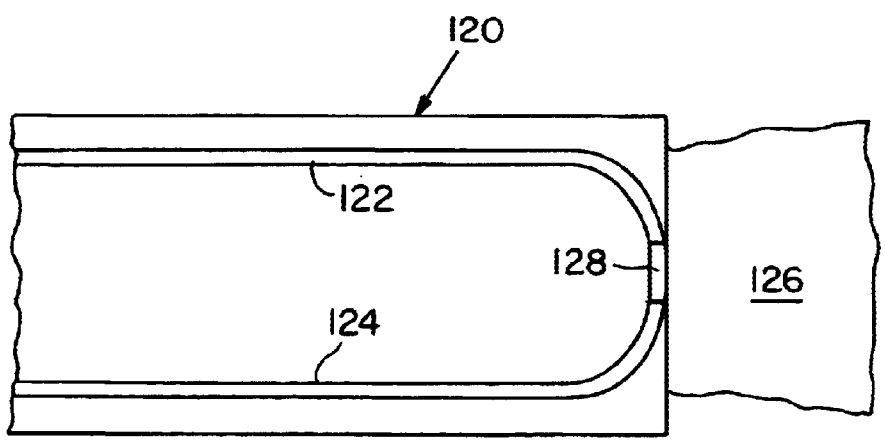

The devices shown in FIGS. 12A and 12B illustrate preferred embodiments of the invention adapted for diagnostic measurements within the human body. In FIG. 12A a single-ended probe 100 is shown where one or more optical fibers 102 both the incident light to, and the transmitted (reflected) light from, the ATR element 104. A 100% infrared reflector 106 such as gold is placed at the distal surface 108 of the ATR element 104 functions to return the transmitted light back through the same fiber as well as to provide double pass sampling. The ATR element 104 can be a separate component optically fastened to the optical fibers 102, or alternatively, it can be constructed from the end of the optical fiber by removing the cladding material. Sampling is provided by placing the ATR element in contact with the tissue 110 of interest. Radiation is transmitted 112 and collected 114 in a radial direction from element 104. The probe can either be inserted through a standard endoscope or catheter to sample a hollow organ, or, if made with sufficiently thin optical fiber, it can be directly inserted directly into a solid organ as in the case of needle biopsy. In this particular embodiment the distal tip 108 is in the form of a needle. The cone or needle configuration on the end of the catheter can be long or shallow.

A double-ended probe is illustrated in FIG. 12B. Incident IR beam from FT-IR is transmitted through IR optical fiber 122 to ATR element 128 positioned at the distal end of catheter body 120. ATR element is placed in contact with tissue 126 surface to be sampled. Transmitted light is conducted through second IR optical fiber 124 back to an IR detector. The ATR element may be a separate component optically fastened to the two optical fibers 122, 124, or it may be simply a region of a single optical fiber in which the fiber cladding material has been removed. The entire apparatus can be inserted through a standard endoscope or outer catheter.

For methods of measuring excised samples, the specimen to be sampled is placed in optical contact with the surface of the waveguide or ATR element. The evanescent wave which extends-outside of the waveguide surface is absorbed by the sample in proportion to its absorption coefficient. The penetration depth of the evanescent wave into the sample depends on the wavelength of the infrared radiation and the refractive indices of the waveguide and the sample; for a ZnSe-water interface, this depth is roughly 1 $\mu$m from 1800 to 700 $cm^{-1}$. The 1/e penetration depth of the evanescent wave into the sample is given by $\lambda/2\pi(n_Z^2 \sin^2 \theta - n_W^2)^{1/2}$, where $\lambda$ is wavelength, $\theta$ is angle of incidence and $n_Z$ and $n_W$ are the refractive indices of ZnSe and water respectively. Consequently, only tissue that is in good optical contact with the ATR element will be sampled. In addition, individual components in the sample can exhibit different affinities for the waveguide material (ZnSe in this case), which can influence the relative concentrations of the components at the waveguide surface. Despite relatively high concentrations in the bulk tissue, components with poor optical contact can be difficult to measure in the ATR spectrum.

Figure 4:
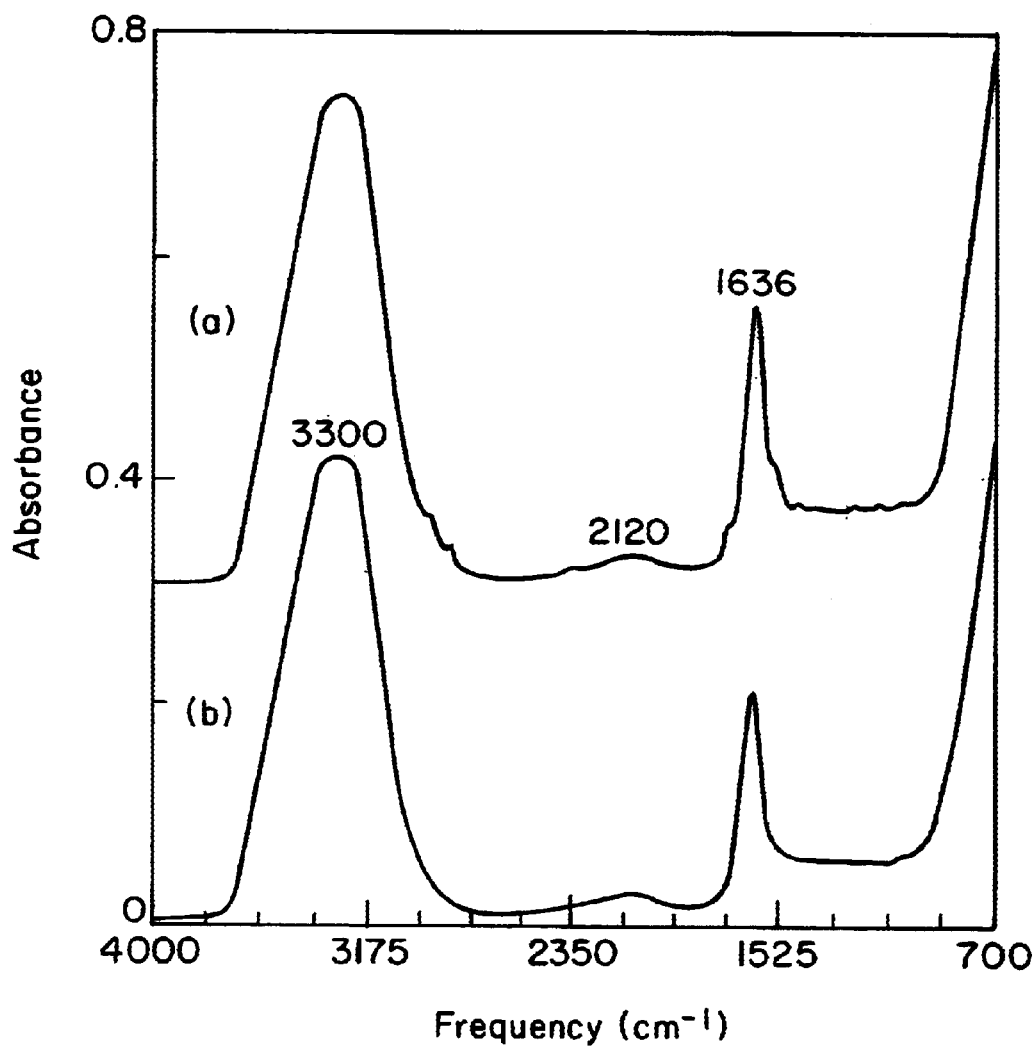
FIG. 4 graphically illustrates FT-IR ATR spectra (4000–700 $cm^{-1}$) of (a) normal aorta, intimal surface; and (b) buffered saline (0.14M NaCl, pH 7.4).

FIG. 4 shows FT-IR ATR spectra of (a) normal aorta (intimal side) and (b) buffered saline. A comparison of these spectra shows that a majority of the IR absorption of normal intima can be attributed to water, which comprises roughly 80% of the tissue by weight. The large, broad bands peaking at 3300 $cm^{-1}$ and 1636 $cm^{-1}$ are due to the O—H stretching and H—O—H bending vibrations, respectively, of water, and the weak band at 2120 $cm^{-1}$ is due to a water combination vibration. The 3300 $cm^{-1}$ and 1636 $cm^{-1}$ bands also include contributions from the N—H stretching and amide I vibrations. The relatively flat absorption between 1500 and 900 $cm^{-1}$ and the rising absorption below 900 $cm^{-1}$ is also due primarily to water; however, in the intima; a number of very weak bands due to other tissue components are also present in this region.

Figure 5:
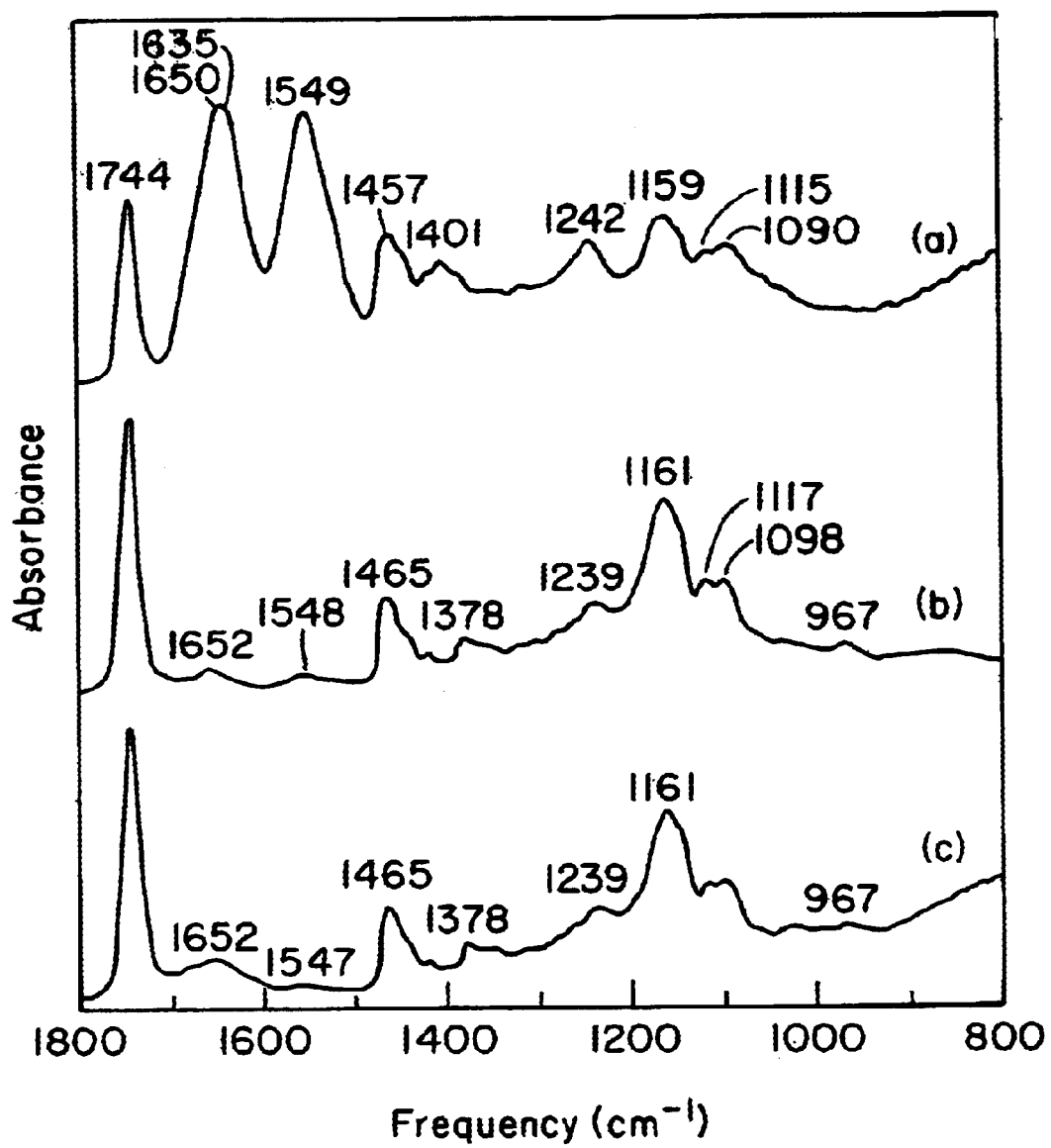
FIG. 5 graphically illustrates FT-IR ATR spectra (1800–800 $cm^{-1}$) after water subtraction: (a) Normal aorta, intimal surface; (b) Sub-adventitial fat; (c) Saline rinsed from the intimal surface of normal aorta.

Most biomolecules give rise to IR absorption bands between 1800 and 700 $cm^{-1}$, which is known as the "fingerprint region" or primary absorption region. The dominant absorption of tissue water in this region obscures the absorption bands from other tissue components. To observe the IR bands from these components, one must eliminate the water interference. With the ATR method, spectral deconvolution or subtraction of the water component is particularly easy. By using the 2120 $cm^{-1}$ band, which is due solely to water, as an internal intensity standard the spectrum of buffered saline (FIG. 4, curve b) can be accurately and reliably subtracted from the spectrum of aorta intima (FIG. 4, curve a), yielding a water-subtracted spectrum of intima (FIG. 5).

In the water-subtracted spectrum, the previously weak bands are easily observed. Band assignments, based on the spectra of the major tissue components are listed in Table I.

TABLE I

Preliminary assignments of IR absorption peaks in the ATR spectra of normal aorta intima.

| $\nu$ ($\pm 1$ $cm^{-1}$) | Preliminary Vibrational Assignment | Associated Tissue Components |
| --- | --- | --- |
| 2923 (s) | C—H stretch | Lipid, Protein, Others |
| 2853 (s) | C—H stretch | Lipid, Protein, Others |
| 1744 (s) | C=O (ester) stretch | Lipid |
| 1651 (s) | Amide I | Protein |
| 1635 (sh) | Amide I, H—O—H bend | Protein, Water |
| 1548 (s) | Amide II | Protein |
| 1465 (s) | $CH_2$ bend | Lipid |
| 1457 (s) | $CH_2$ bend, $CH_3$ antisymmetric deformation | Lipid |
| 1454 (m) | CH bend, $CH_3$ antisymmetric deformation | Protein, others |
| 1417 (w) | $CH_2$ bend adjacent to C=O | Lipid |
| 1401 (m) | COO— symmetric stretch, amide C—N stretch | Protein, others |
| 1378 (w) | $CH_3$ symmetric deformation | Lipid |
| 1244 (m) | Amide III, $PO_2$— antisymmetric stretch | Protein, others |
| 1239 (m) | $CH_2$ wag, $PO_2$— antisymmetric stretch | Lipid |
| 1159 (s) | $CH_2$ wag, C—O—C antisymmetric stretch | Lipid |
| 1117 (w) | C—C stretch, O—C—O stretch | Lipid |
| 1096 (w) | | Lipid |
| 1083 (w) | $PO_2$— symmetric stretch | Protein, others |
| 1030 (w) | | Lipid |
| 965 (w) | C=CH deformation (trans) | Lipid |
| 722 (m) | $CH_2$ rock | Lipid |

Most of the vibrational bands observed in the spectrum of normal intima (FIG. 5, curve a) can be divided into two broad categories: lipid-associated bands and protein-associated bands. All of the strong bands in normal intima are associated with one of these moieties (see Table I). This can be seen as a simple consequence of the large concentrations of these two materials. Aside from water, a large fraction of tissue can be divided into one of these two groups. Moverover, both protein and lipid components contain repeating molecular units which are common to all members of the group. For protein, the polypeptide backbone of repeating amide groups is the dominant element. In lipids, the repeating hydrocarbon chain is the defining quality. The end result is that these molecular units are present in very large concentrations, and their vibrational bands tend to dominate the spectrum. Note that this does not imply that no further level of detail is derivable from the IR spectrum of tissue. For example, the frequencies of the amide group vibrations are sensitive to protein configuration and conformation. Therefore, shifts in protein makeup might be expected to produce observable changes in the amide bands.

The water-subtracted spectrum of sub-adventitial fat shown in FIG. 5, curve b, more clearly illustrates the division of bands into lipid and non-lipid categories. This fat can be considered as the model of the lipid component. Protein contributions, as judged from the intensities of the amide I and II bands, are negligible for the purposes of this model. All of the bands observed in the fat spectrum can be attributed to the lipid component. These include the strong bands at 1744 cm$^{-1}$ (C=O stretch), 1465 cm$^{-1}$ (C—H bend), 1161 cm$^{-1}$ (CH$_2$ wag, C—O—C stretch), as well as the weaker bands at 1378 cm$^{-1}$, 1239 cm$^{-1}$, 1118 cm$^{-1}$, 1099 cm$^{-1}$, 966 cm$^{-1}$, and 722 cm$^{-1}$.

Figure 6:
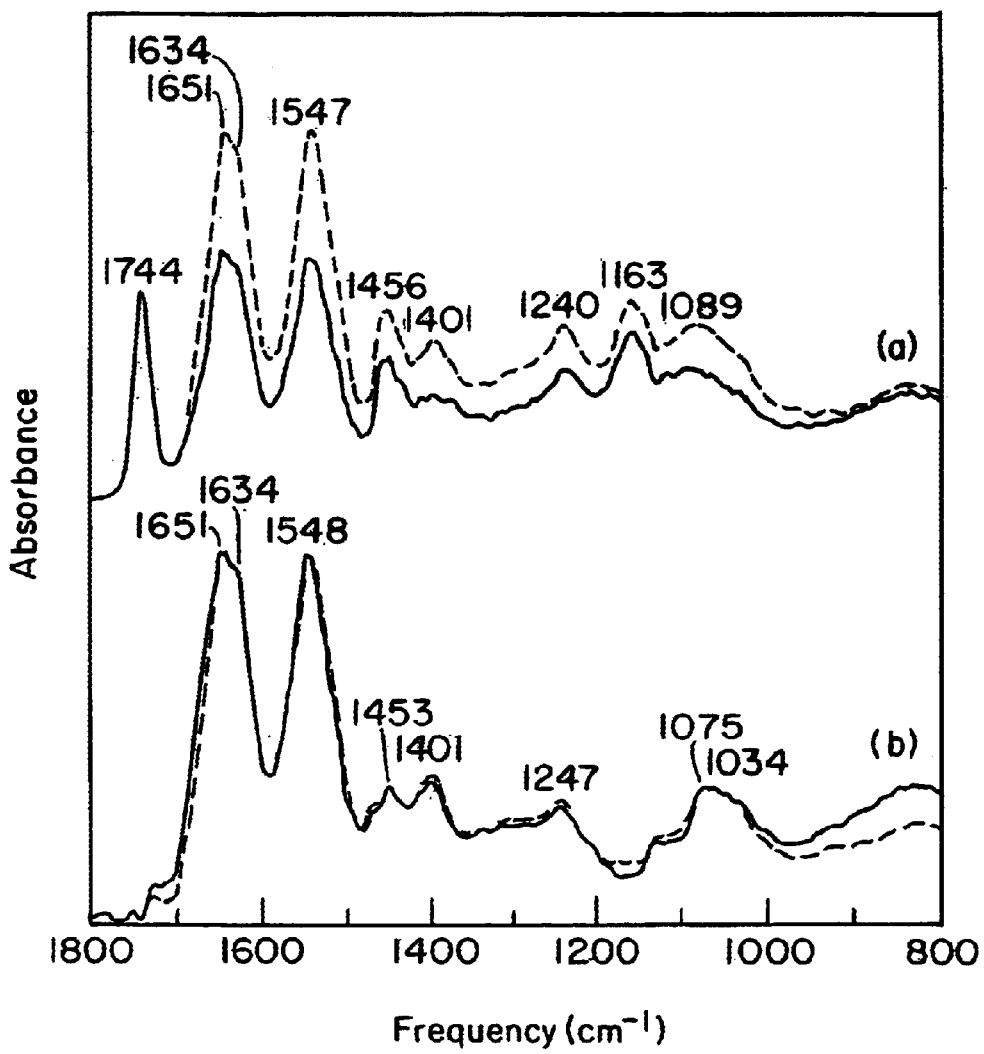
FIG. 6 graphically illustrates FT-IR ATR spectra (1800–800 $cm^{-1}$): (a) Two consecutive water-subtracted spectra of normal aorta, intimal surface, collected immediately after placement on ATR element (solid line) and 10 minutes later (dashed line); (b) Same two spectra as in (a) after lipid subtraction, scaled to have equal maxima.

The bands observed in the water-subtracted spectrum of intima constitute less than 30% of the total absorption, the rest being due to water. Any conclusions regarding these relatively weak bands depends critically upon the accuracy of the water substraction. The accuracy of this subtraction can be judged from the reproducibility of spectra obtained sequentially from the same sample. Two consecutive water-subtracted spectra collected 10 minutes apart from a sample of normal aorta (intimal side) are shown in FIG. 6, curve a (solid and dashed curves). Most of the IR bands exhibit a substantial increase in absorbance with time. This trend continues for consecutive spectra collected more than an hour after the placement of the sample on the ATR element. However, not all of the bands change by the same fraction, so that the relative intensities differ between consecutive spectra. For instance, in FIG. 6, curve a, the C=O band at 1744 cm$^{-1}$ is relatively constant, while the amide bands at 1650 cm$^{-1}$ and 1547 cm$^{-1}$ increase by 50% in the later spectrum. Although these changes might seem to indicate that the water subtraction is inaccurate, the changes with time are systematic and predictable, which suggests that the optical contact between the sample and the ATR element is changing regularly with time.

In fact, the constancy of the 1744 cm$^{-1}$ C=O band, which is due solely to lipid, and the increases in the amide bands, which are due to protein, indicate that the lipid contributions to the IR absorption remain unchanged while the non-lipid contributions increase between consecutive scans. This is confirmed by subtracting the spectrum of lipid (FIG. 5, curve b) from the water-subtracted spectra of aorta intima (FIG. 6, curve a), using the 1744 cm$^{-1}$ band for normalization. The resulting lipid-subtracted spectra of aorta intima are shown, normalized to peak absorbance, in FIG. 6, curve b. As can be seen, the relative peak absorbances and spectral bandshapes in the lipid-subtracted spectra reproduce quite well, reflecting the accuracy of both the water and the lipid-subtration procedures.

The constancy of the lipid bands and the variation of the non-lipid bands between successive scans may seem somewhat puzzling. An explanation of this apparent anomaly can be inferred from a water-subtracted spectrum of saline solution which is rinsed off the surface of the tissue (FIG. 5, curve c). This spectrum, aside from the weak amide I and II bands, matches quite closely with that of adventitial fat. The lipid component observed in the tissue appears to be due to free lipid particles that have equilibrated with the tissue surface water, forming a thin water-lipid film on the tissue surface which is in full optical contact with the ATR element immediately after the tissue specimen is placed upon the crystal. The tissue components beneath this film presumably achieve better optical contact with the ATR crystal, as the sample settles. As a result, the content of lipid in a spectrum of aorta intima or media may be influenced by the presence of sub-adventitial fat in the specimen, and the relative lipid-protein absorbances are accurate to 50% at best with the present experimental design. For the reason, all of the remaining spectra shown are both water and lipid subtracted.

With the lipid bands removed, assessment of the non-lipid bands in the spectrum of normal intima (FIG. 6, curve b) is greatly simplified. The major bands in the spectrum may be assigned to protein backbone vibrations. These include the bands at 1648 cm$^{-1}$ (amide I), 1549 cm$^{-1}$ (amide II), 1455 cm$^{-1}$ (C—H bend), 1401 cm$^{-1}$ (amide C—N stretch), and 1244 cm$^{-1}$ (amide III). The frequency of the amide I peak (1648 cm$^{-1}$), which is sensitive to protein secondary structure, may indicate contributions from α-helix, disordered, and collagen helix conformations. This band also exhibits a shoulder near 1634 cm$^{-1}$, which may be due to the β-sheet regions of proteins or water. The protein C—H bending band at 1455 cm$^{-1}$ is distinct from the corresponding vibration in lipid, which occurs as a double-peaked band at 1465/1457 cm$^{-1}$. Note that all of these bands may include contributions from other moieties. For instance, the symmetric stretch of carboxylate groups and the antisymmetric stretch of phosphate groups may also contribute, respectively, to the 1401 cm$^{-1}$ and 1244 cm$^{-1}$ bands. This correlation of components is summarized in Table I above.

Figure 7:
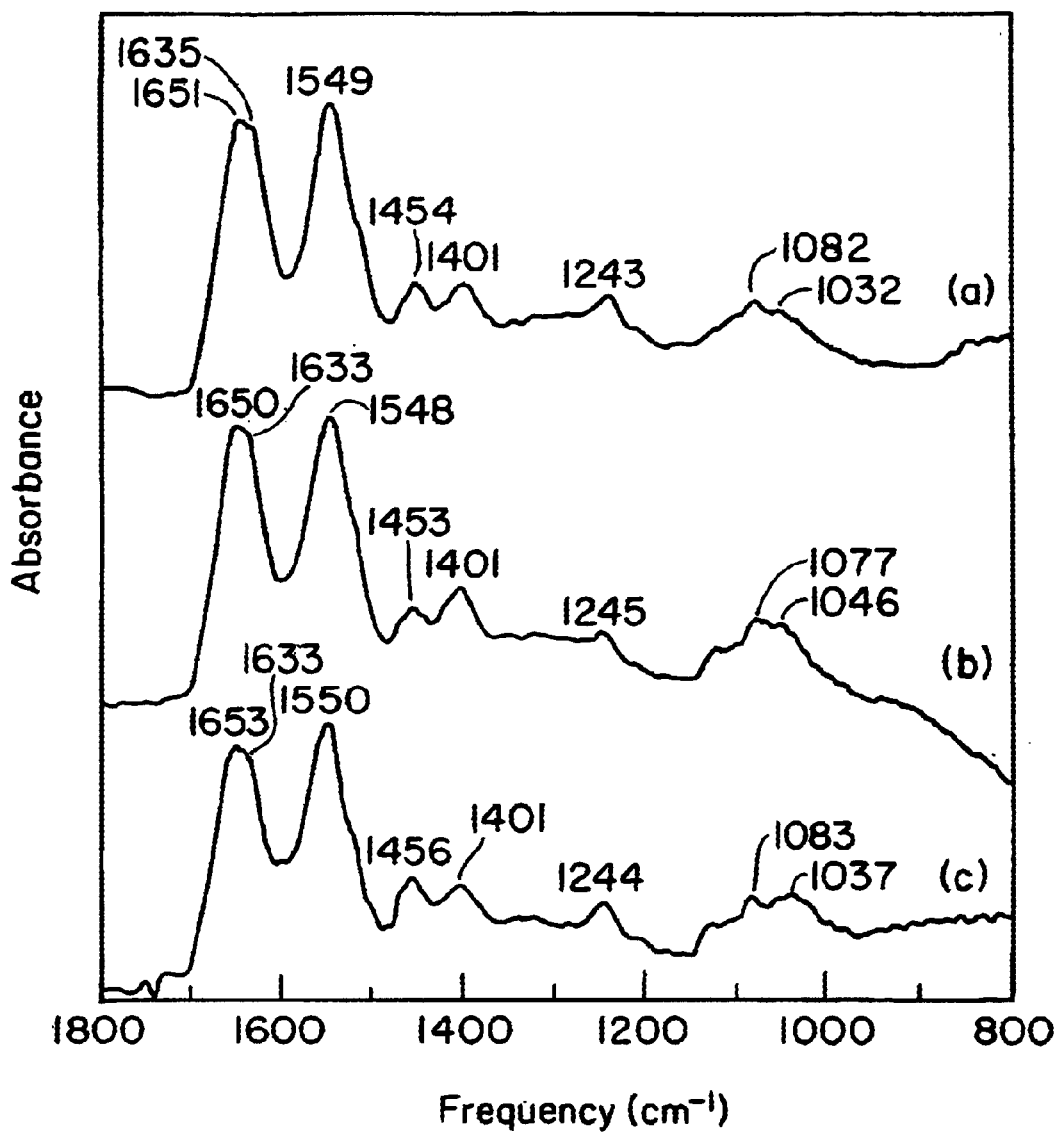
FIG. 7 graphically illustrates FT-IR ATR spectra (1800–800 $cm^{-1}$), water-and lipid-subtracted: (a) Normal aorta, media layer; (b) Atherosclerotic plaque; intimal surface; (c) Atheromatous plaque with intact fibrous cap, intimal surface.

A typical spectrum of the medial layer of normal aorta is shown in FIG. 7, curve a. A comparison of this spectrum to that of normal intima (FIG. 6, curve b) fails to reveal any significant differences. This result is somewhat surprising, considering that normal aorta intima and media have significantly different compositions. Typical spectra of an atherosclerotic plaque and a non-ulcerated atheromatous plaque are shown in FIGS. 7, curve b and c, respectively. For these plaques, only the intact fibrous cap at the intimal surface is probed due to the short penetration depth (1 μm) of the beam. Any necrotic, atheromatous material beneath this fibrous cap is not sampled. Even so, the fibrous caps of these plaques are known to be compositionally different than normal intima and one might expect these differences to be reflected in the IR ATR spectrum. However, as in the case of media, no consistent differences are observed in the spectra of these plaques (FIGS. 7, curve b and c) and normal intima (FIG. 6, curve b). This issue will expanded upon in the discussion below.

On the other hand, substantial differences are obvious in the spectrum of the necrotic, atheromatous core of an atheromatous plaque (FIG. 8a) as compared with the corresponding spectra of normal intima (FIG. 6, curve b) as well as those of intact atherosclerotic (FIG. 7, curve b) and atheromatous (FIG. 7, curve c) plaques. In this case, the necrotic core was presumably exposed in vivo as disease progressed by ulceration of the overlying intimal fibrous tissue cap. (The spectrum of necrotic core exposed by dissecting away the fibrous cap of a non-ulcerated atheromatous plaque is similar.) A new band appears at 1050 cm$^{-1}$, with a secondary peak at 1023 cm$^{-1}$. In addition, the necrotic core spectrum exhibits an increase and frequency shift in the 1466 cm$^{-1}$ band as compared with the 1455 cm$^{-1}$ protein band in normal intima as well as a set of unique bands near 1382 cm$^{-1}$. These characteristic bands are found in the spectra of all the exposed necrotic core samples and in none of the other samples (see below).

Figure 8:
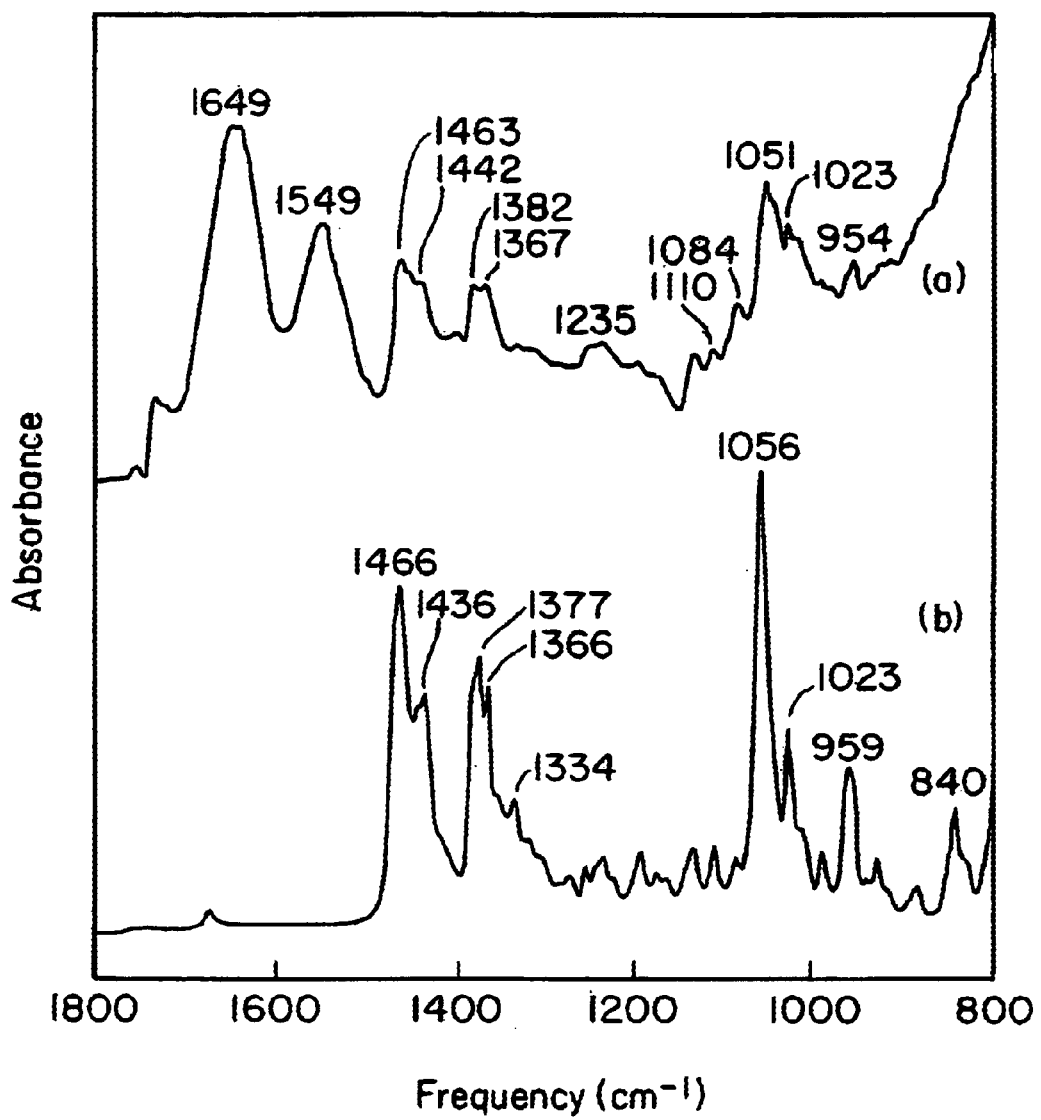
FIG. 8 graphically illustrates FT-IR ATR spectra (1800–800 $cm^{-1}$): (a) Necrotic core of atheromatous plaque, water-and lipid-subtracted; (b) Dry film of cholesterol.

The source of these unique bands in the necrotic core spectra may be cholesterol, which is known to accumulate in large amounts in atheromatous cores. An ATR spectrum of cholesterol (dry film) is shown in FIG. 8, curve b. The three major bands unique to the necrotic core, near 1463 cm$^{-1}$, 1382 cm$^{-1}$, and 1050 cm$^{-1}$, match closely in position and relative intensities with the three main cholesterol bands at 1466 cm$^{-1}$, 1377 cm$^{-1}$, and 1056 cm$^{-1}$. Each of the main cholesterol bands has a secondary peak, which also appear to be present in the necrotic core bands. These secondary peaks occur at 1445/1436 cm$^{-1}$, and 1023 cm$^{-1}$ in the cholesterol spectrum and at 1441 cm$^{-1}$, 1367 cm$^{-1}$ and 1023 cm$^{-1}$ in the necrotic core spectrum. In addition, several of the weak bands in the necrotic core spectrum, including the peaks at 1334 cm$^{-1}$, 1109 cm$^{-1}$, 954 cm$^{-1}$, and 797 cm$^{-1}$, are associated with the weaker cholesterol bands near these frequencies. Other components in the necrotic core may also contribute to some of these distinct bands.

Figure 9:
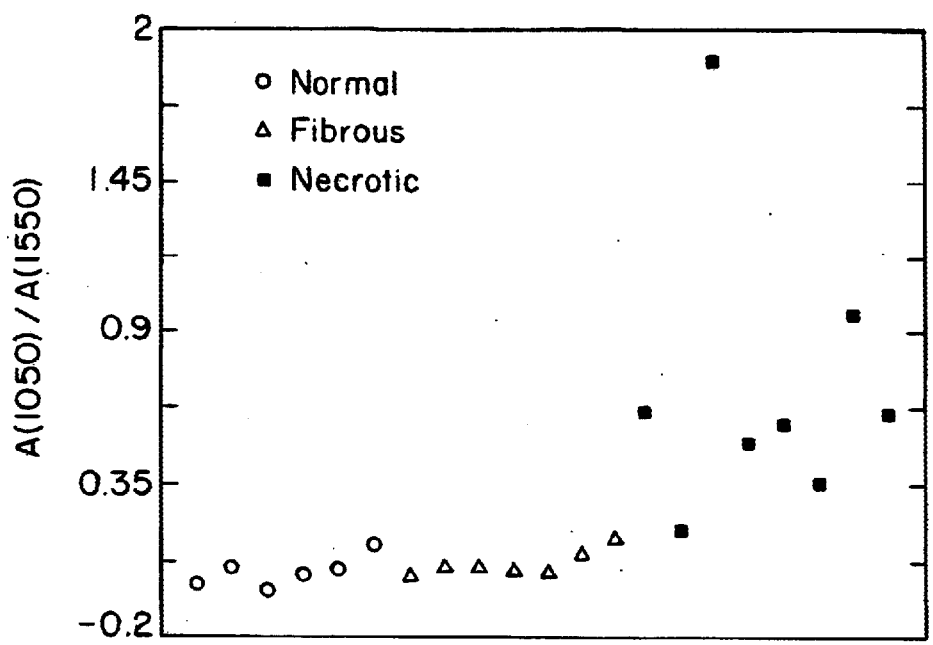
FIG. 9 graphically illustrates scatter plot for all samples of the area, A(1050), of the 1050 $cm^{-1}$ cholesterol band (integrated from 1075 to 1000 $cm^{-1}$) ratioed to the area, A(1550) of the 1548 $cm^{-1}$ protein amide II band (integrated from 1593 to 1485 $cm^{-1}$). The intensities were calculated from the water-and lipid-subtracted spectra. NORMAL denotes normal aorta specimens, intimal side, FIBROUS includes atherosclerotic and atheromatous plaques with intact fibrous caps, and NECROTIC includes exposed necrotic atheroma cores and necrotic material isolated from atheromatous plaques.

The consistency of the spectral differences which are attributed to cholesterol between the necrotic core specimens and the normal, atherosclerotic, and non-ulcerated atheromatous specimens are illustrated in the scatter plot in FIG. 9. This plot depicts the integrated intensities (areas) of the 1050 cm$^{-1}$ cholesterol band ratioed to the total protein content, as measured by the area of the amide II band at 1548 cm$^{-1}$. The 1050 cm$^{-1}$ band was integrated from 1075 to 1000 cm$^{-1}$ and baseline subtracted using these endpoints, and the amide II band was integrated from 1593 to 1485 cm$^{-1}$ with a similar baseline subtraction. This ratio is a measure as the relative cholesterol contribution to the spectrum, and is proportional to the relative cholesterol concentration of the sample with the assumption that the area of the 1050 cm$^{-1}$ band is due soley to cholesterol. As can be seen in FIG. 9, this ratio is higher for all the exposed necrotic core specimens than for all the other specimens. The consistent results of this sample analysis, which is possible because of the separation and molecular identification of the bands, indicates the potential of IR spectroscopy for tissue characterization.

Investigations of human arteries and atherosclerosis by mid-IR spectroscopy have been limited to date. It has been reported that ATR spectra have been recorded from partially dried human artery, among other tissues. In comparing a normal aorta from an infant to an atherosclerotic plaque in an adult, they observed increases in several bands in the atherosclerotic aorta. Most of these bands were associated with lipids and lipoproteins. IR spectroscopy has been employed to determine the chemical composition of calcified atherosclerotic deposits. A more detailed IR study of atherosclerotic aorta involves recorded IR transmission spectra from thin layers sectioned at different depths into the arterial wall. Results showed increased absorption near 1739 cm$^{-1}$ in the fatty (atheromatous) regions of plaque, which was attributed to absorption by cholesterol esters in the plaque. IR spectra from the fibrous tissue cap at the surface of the plaques were similar to normal intima.

One of the main difficulties in measuring mid-infrared spectra of intact human tissue is the intense water absorption, which domirates and obscures the absorption of other tissue components of interest. In nost of the studies cited above, the water absorption was not eliminated, limiting the quality and amount of information available from the spectra. With the ATR sampling method, this water interference is easily removed (see FIG. 5). The ATR method is also naturally amenable to sampling with fiber optic probes in vivo. Water interference in fiber optic probe ATR spectra of aqueous protein solutions has been accurately eliminated with a water subtraction procedure similar to the one employed in the present study.

While the ATR method is well suited to in vivo sampling and to accurate subtraction of the water signal, spectra collected with the ATR method are not equivalent to IR absorption spectra, but depend on properties of the ATR material and the sample in addition to the sample absorption coefficient. For instance, the penetration depth of the evanescent sampling wave depends on the refractive indices of the ATR material and the sample. However, the refractive indices of both ZnSe and human tissue are expected to vary slowly with frequency between 1800 and 700 cm$^{-1}$ and such variations will at most affect the relative intensities of bands at different frequencies. All of the structure observed in the tissue spectra is attributed to absorption bands in the tissue.

The component absorptions observed in an ATR spectrum also depends upon the optical contact of the sample and ATR element. The small penetration depth of the evanescent wave into the tissue sample implies that only a 5 $\mu$m thick layer, and preferably about 1 micron, of material at the surface is observed. This is refered to as the near surface region of the tissue for the purposes of this application. The tissue deeper than 5 microns from the surface is defined as the sub-surface region. This thin, sampled near-surface layer may differ in composition with the bulk sample. For example, a film of free water may be present on the surface of wet tissue, with different levels of some molecular species of the tissue relative to their concentrations in the bulk tissue. In addition, the varied affinities for the ATR material of different moieties in the tissue may play an important role in the intensities of the observed bands.

These considerations may explain the lack of substantial differences among the ATR spectra of normal intima, plaque fibrous cap, and media. For instance, normal aorta intima is composed of roughly 25% collagen (dry weight) and 20% elastin, while aorta media has 20% collagen and 50% elastin. The ATR spectra of purified collagen and purified elastin (not shown) differ substantially. In particular, amide I/II occur at 1657/1556 cm$^{-1}$ in hydrated collagen (type I) and 1653/1543 cm$^{-1}$ in hydrated elastin (spectra not shown).

One might expect these differences to be reflected in the intima and media ATR spectra. A possible explanation of why this is not the case is that the thin layer in optical contact wit the ATR element is compositionally different from the bulk tissue, and collagen and elastin make only a minor contribution to the IR ATR bands of this layer. Such an effect may also explain the lack of significant differences among the plaque fibrous cap intima and normal intima ATR spectra. In ATR elements made of other substances with different biochemical affinities, the spectral differences among these tissues might be substantially enhanced.

The results of the present investigation demonstrate that high quality water-subtracted spectra can be readily obtained from human tissue with the ATR technique. Similar results have been obtained in other mammalian tissues. Accurate removal of the water interference is crucial to isolating the relatively weak tissue absorption bands of lipid, protein, as well as other tissue components. It is worth noting that the observation of these relatively weak bands via spectral subtraction depends entirely upon quality of the tissue and saline spectra. For instance, the absorbance of the normal intima specimen (FIG. 4, curve a) between 1500 and 900 cm$^{-1}$ is approximately 0.06. In the water-subtracted spectrum (FIG. 5, curve a), the peak absorbances range from 0.018 (30%) for the strongest bands to 0.003 (5%) for the weakest ones. The detection of a 0.003 absorbance peak in a subtracted spectrum with a 0.06 absorbance background requres a signal-to-noise ratio of 700 or better in the 100% baseline. Such a signal-to-noise is easily achieved with an FT-spectrometer. The high linearity, baseline stability, and wavelength precision of the FT-spectrometer are also obviously critical for accurate background subtraction.

While water subtraction is relatively easy and accurate with ATR, it may be substantially more difficult with other clinically applicable sampling techniques such as diffuse reflectance or photoacoustic sampling. These alternative sampling techniques are clinically useful, however, because of their longer tissue penetration depths (approximately 10 $\mu$m). As an alternative to water subtraction, one can exploit the properties of the spectral lineshape of water to eliminate the water signal by other computational methods. Specifically, the spectral lineshape of water varies rather slowly with frequency over much of the region of interest, especially between 1500 and 700 cm$^{-1}$. Therefore, any transformation which filters this slower variation and spares the sharper features of the non-water bands can separate the water and non-water components.

Figure 10:
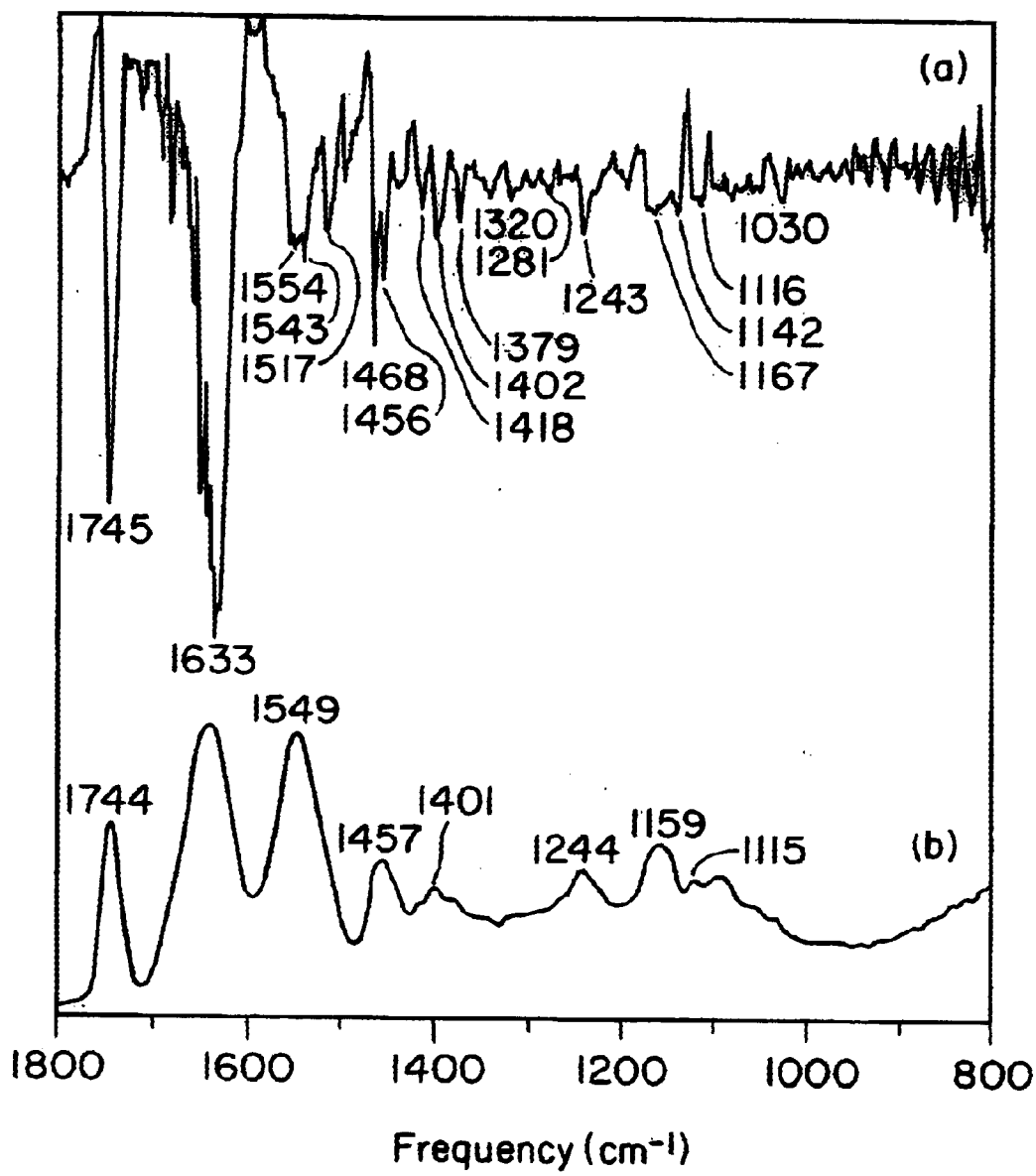
FIG. 10 graphically illustrates FT-IR ATR spectra (1800–800 $cm^{-1}$): (a) Second derivative spectrum of normal aorta intima (FIG. 4a); (b) Water-subtracted spectrum of same normal aorta intima specimen (same as FIG. 5a).

One such method is second derivative spectroscopy. Differentiation of a spectrum is typically used to narrow absorption bands and resolve overlapping peaks. Differentiation also tends to deemphasize broad bands relative to sharper ones. In IR spectra of artery, the broad, featureless absorption of water can be nearly eliminated in favor of the sharper non-water bands by computing the second derivative of the spectra. This is clearly demonstrated in FIG. 10, which shows the second derivative of a spectrum of normal aorta intima (FIG. 10, curve a), along with the water-subtracted spectrum of the same specimen (FIG. 10, curve b). Essentially only the 1633 cm$^{-1}$ water band is left, partially obscuring the amide I band. Elsewhere in this spectrum, the water contribution is minimal. All of the bands identified in the water-subtracted spectrum are easily observed in the second derivative spectrum.

In addition to elimination of water interference, several of the unresolved double peaks and shoulders in the water-subtracted spectrum appear as distinct peaks in the second derivative spectrum. For example, the amide II band in normal intima (FIG. 10, curve b) has a very weak shoulder near 1518 cm$^{-1}$, and the C—H bending region near 1468 cm$^{-1}$ appears to include two overlapping peaks. In the second derivative spectrum (FIG. 10, curve a), the 1518 cm$^{-1}$ band is clearly visible, and the C—H region exhibits two separate peaks at 1469 and 1456 cm$^{-1}$. Moreover, by sharpening the bands, the second derivative spectrum allows a more precise determination of peak frequencies, so that relatively small frequency shifts are observed. Such frequency shifts can be of importance in detecting and characterizing subtle molecular alterations involved in certain tissue conditions.

The observation of individual, resolved bands in the artery IR ATR spectra is of considerable interest, since separation of bands is the first step determining the composition of a sample from its spectrum. Once a band has been isolated, its integrated intensity is proportional to the concentration of the moiety responsible for that band. In particular, since the amide I and II bands are due entirely to protein, these bands can be used to isolate the overall protein content in the spectrum. The sharp, well resolved 1744 cm$^{-1}$ C=O ester band appears to be due to solely to lipid, and the integrated intensity of this band should be proportional to the relative lipid content are technique should largely eliminate the inaccuracies. Finally, it should be remembered that the relative water content of the tissue sample is automatically computed from the 2120 cm$^{-1}$ band in the water subtraction algorithm. However, as noted earlier, the composition of tissue as determined from an ATR spectrum may not be precisely identical to the composition of the bulk tissue.

The tissue composition can also be determined from overlapping bands by first deconvolving the bands of interest into their individual components. This is especially easy if one component has an additional, isolated band elsewhere in the spectrum. An example is the 1465 cm$^{-1}$ C—H bending region, which is due to different tissue components with distinct spectral features in this region. In the normal intima spectrum (FIG. 5a), this band is attributed to a combination of lipid and protein components. Since the lipid component also exhibits the isolated 1744 cm$^{-1}$ band, this band can be used to subtract the lipid C—H bending component and isolate the protein C—H bending component at 1455 cm$^{-1}$ (FIG. 6b), effectively deconvolving this band. Note that this deconvolution depends on having a reliable spectrum of one of the individual components, which, in this example, is the lipid spectrum in FIG. 5b.

Figure 11:
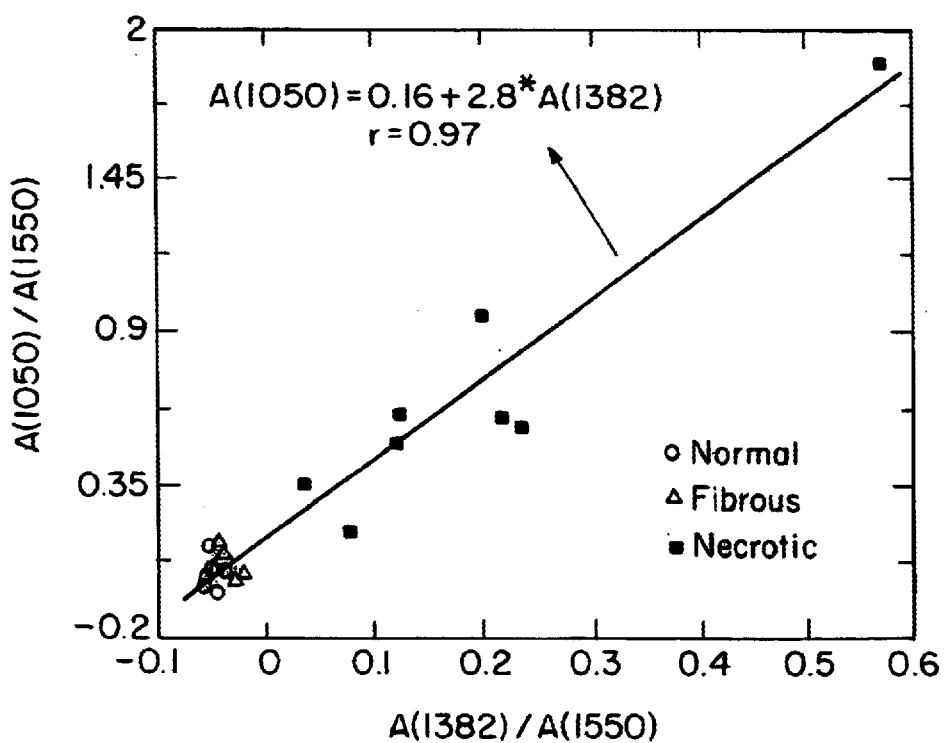
FIG. 11 graphically illustrates a scatter diagram for all the specimens of the area, A(1050) of the 1050 $cm^{-1}$ cholesterol band plotted versus the area, A(1382), of the 1382 $cm^{-1}$ cholesterol band. Both cholesterol bands have been normalized to the area, A(1050), of the protein amide II band. All band intensities were calculated from the water-and lipid-subtracted spectra. Tissue categories are the same as in FIG. 9. The solid line represents a linear least squares fit to the data.

The detection of distinct bands attributed to cholesterol in necrotic core may provide a useful means of determining cholesterol concentrations in vivo. Both the 1050 cm$^{-1}$ and 1382 cm$^{-1}$ cholesterol bands appear to be fairly isolated in the necrotic core spectrum after lipid-subtraction (FIG. 8). If these two bands are due to a single component, namely cholesterol, the ratio of their integrated intensities should be a constant for all the samples. The baseline-subtracted area of the 1050 cm$^{-1}$ band, A(1050), is plotted versus that of the 1382 cm$^{-1}$ band, A(1382), for all the samples, normalized to the protein content in FIG. 11. As can be seen in the plot, there is a roughly linear relationship between A(1050) and A(1382). A linear least squares fit to this data yields the line shown in the plot, with a high regression coefficient of r=0.967. The slope of this line 2.8, while the ratio A(1050)/A(1382) for the pure cholesterol ATR spectrum is 2.3. The reasonable agreement between these two numbers provides additional evidence for the assignment of these bands to cholesterol. Moreover, it indicates that the relative spectral content of cholesterol is reasonably approximated by the integrated intensities of either of these bands. FIG. 11 also shows that the ATR spectra of all the specimens other than exposed necrotic core exhibit almost no intensity in both the 1050 and 1382 cm$^{-1}$ bands, in contrast to the necrotic specimens, all of which have significant bands at both frequencies.

The present systems and methods demonstrate that infrared spectra of moist, bulk tissues can be reliably obtained with the ATR technique. Although water is the dominant absorber throughout much of the mid-infrared region, the high quality spectra acquired with the FT-IR ATR technique allow for accurate subtraction of the water signal. Elimination of the water interference is critical for identifying and assigning the absorption bands of other tissue species. The isolation and designation of these relatively sharp bands provides a means of analyzing spectroscopically the composition of arterial tissue non-destructively. There methods are also applicable to the study and diagnosis of other tissues and tissue conditions, such as neoplasia.

The observation of both lipids and cholesterol in the spectra of necrotic atheromatous core samples is particularly exciting, because lipids and cholesterol are thought to play major roles in the pathogenesis of atherosclerosis. The spectral observation of these components, cholesterol in particular, provides a reliable means of detecting and characterizing advanced atheromatous plaques in which ulceration of the fibrous cap has occurred (as demonstrated in FIGS. 9 and 11). Intimal accumulations of lipid and cholesterol occur early in the atherogenic process. Therefore, the mid-IR ATR technique can also be useful in detecting and studying the early fatty streak lesion.

Equivalents

Those skilled in the art will recognize, or be able to ascertain using routine experimentation, many equivalents to the specific embodiments of the invention described herein. These and all other equivalents are intended to be encompassed by the following claims.

What is claimed is:

1. A method of spectroscopic diagnosis of tissue comprising:

irradiating a subsurface portion of atherosclerotic tissue within a vascular lumen to be diagnosed with radiation having a frequency within the infrared range transmitted through a fiber optic cable;

detecting light emitted by the portion of atherosclerotic tissue in response to the radiation, the light having a plurality of Raman shifted frequencies in a range of 750 $cm^{-1}$ to 1750 $cm^{-1}$ that are different from the irradiating frequency; and analyzing the plurality of Raman shifted frequencies of detected light to diagnose the tissue including the step of comparing the detected light with reference data to determine the presence of a fibrous tissue cap overlying a calcified layer.

2. The method of spectroscopic diagnosis of claim 1 wherein the detecting step further comprises collecting the emitted light through the fiber optic cable.

3. The method of spectroscopic diagnosis of claim 2 wherein the coupling step further comprises providing a catheter for insertion into body lumens.

4. The method of spectroscopic diagnosis of claim 2 wherein the fiber optic cable receives light emitted by the tissue and transmits the emitted light to a spectroscopic analysis system.

5. The method of spectroscopic diagnosis of claim 4 further comprising providing a fourier transform spectrometer to receive the emitted light.

6. A method of spectroscopic diagnosis of arterial tissue comprising:

positioning a catheter containing a light transmitting fiber optic cable adjacent to a portion of tissue within an artery to be diagnosed;

irradiating the portion of tissue with radiation having a frequency within the infrared range;

collecting light emitted by the portion of tissue in response to the radiation with the catheter, the light having a plurality of Raman shifted frequencies different from the irradiating frequency;

transmitting the collected light to a proximal end of the catheter;

detecting the collected light including the plurality of Raman shifted frequencies with a detector in a range of 750 $cm^{-1}$ to 1750 $cm^{-1}$; and analyzing the plurality of Raman shifted frequencies of detected light received at the proximal end to diagnose the tissue including the step of comparing the detected light with reference data to determine the presence of a fibrous tissue cap overlying a calcified layer.

7. The method of spectroscopic diagnosis of claim 6 wherein the fiber optic cable receives light emitted by the tissue and transmits the emitted light to a spectroscopic analysis system.

8. The method of spectroscopic diagnosis of claim 7 further comprising providing a fourier transform spectrometer.

* * * * *

UNITED STATES PATENT AND TRADEMARK OFFICE
CERTIFICATE OF CORRECTION

| | |
|---|---|
| PATENT NO. | : 6,697,665 B1 |
| DATED | : February 24, 2004 |
| INVENTOR(S) | : Richard P. Rava et al. |

It is certified that error appears in the above-identified patent and that said Letters Patent is hereby corrected as shown below:

<u>Column 17,</u>
Lines 39-41, should read as follows:
-- 3. The method of spectroscopic diagnosis of claim 2 further comprising providing a catheter for insertion into body lumes. --.

Signed and Sealed this

Twenty-eighth Day of June, 2005

JON W. DUDAS
*Director of the United States Patent and Trademark Office*